(12) United States Patent
Tomazi

(10) Patent No.: US 7,495,098 B2
(45) Date of Patent: Feb. 24, 2009

(54) EXTRACTION OF ALKALOIDS FROM OPIUM

(75) Inventor: Keith G. Tomazi, Florissant, MO (US)

(73) Assignee: Mallinckrodt Inc, Hazelwood, MO (US)

( * ) Notice: Subject to any disclaimer, the term of this patent is extended or adjusted under 35 U.S.C. 154(b) by 225 days.

(21) Appl. No.: 11/578,627

(22) PCT Filed: May 6, 2005

(86) PCT No.: PCT/US2005/016512

§ 371 (c)(1),
(2), (4) Date: Oct. 16, 2006

(87) PCT Pub. No.: WO2005/123743

PCT Pub. Date: Dec. 29, 2005

(65) Prior Publication Data

US 2007/0241065 A1    Oct. 18, 2007

Related U.S. Application Data

(60) Provisional application No. 60/577,801, filed on Jun. 8, 2004.

(51) Int. Cl.
C07D 489/02    (2006.01)
(52) U.S. Cl. ......................... 546/44; 514/282
(58) Field of Classification Search .................. 546/44; 514/282; 210/773
See application file for complete search history.

(56) References Cited

U.S. PATENT DOCUMENTS 1,048,712 A    12/1912    Lloyd

| 1,234,729 | A | 10/1917 | Gams |
| 5,922,876 | A | 7/1999 | Huang et al. |
| 6,262,266 | B1 | 7/2001 | Chiu et al. |
| 6,376,221 | B1 | 4/2002 | Fist et al. |
| 2002/0045755 | A1 | 4/2002 | Coop et al. |
| 2002/0106761 | A1 | 8/2002 | Fist et al. |
| 2003/0087306 | A1 | 5/2003 | Christensen et al. |
| 2003/0124086 | A1 | 7/2003 | Bentley et al. |

FOREIGN PATENT DOCUMENTS

| CA | 504758 | 8/1954 |
| DE | 308151 | 6/1915 |
| DE | 205121 | 5/1978 |
| DE | 2726925 | 12/1978 |
| FR | 1268401 | 12/1947 |
| GB | 27378 | 0/1912 |
| GB | 114190 | 3/1917 |
| WO | WO 95/01984 | 1/1995 |

OTHER PUBLICATIONS

Heumann et al., "The manufacture of alkaloids from opium", Bulletin on Narcotics, 1957, vol. 9, No. 2, pp. 34-40, XP002345736.

*Primary Examiner*—Janet L. Andres
*Assistant Examiner*—David E Gallis

(57) ABSTRACT

A method for extracting at least one alkaloid from opium that includes dissolving opium in a solvent, heating the dissolved opium solution, cooling the dissolved opium solution, adjusting the pH of the dissolved opium solution with at least one first weak acid, filtering the dissolved opium solution to recover a filtrate; and then separating and purifying at least one alkaloid in the filtrate. Preferably, this includes an additional step of chilling the opium solution after adjusting the pH of the dissolved opium solution with at least one first acid. The preferred method for separating and purifying at least one alkaloid in the filtrate includes utilizing preparative liquid chromatography, however, solvent extraction and filtration can also be utilized.

23 Claims, 2 Drawing Sheets

EXTRACTION OF ALKALOIDS FROM OPIUM

CROSS REFERENCE TO RELATED APPLICATIONS

This application is a national stage application of PCT/US2005/016512, filed May 6, 2005, which claims the benefit of U.S. Provisional Application No. 60/577,801 filed Jun. 8, 2004.

BACKGROUND OF THE INVENTION

Opium is a key material that is used in the production of morphine, codeine, thebaine and narcotine. Moreover, it is the only source for narcotine. Opium is obtained by cutting the unripe pods of *Papaver Somniferum*, then collecting the resulting fluid and drying the fluid under ambient conditions. Opium is typically obtained in loaves that are individually wrapped in paper and is a black, tarry material with a characteristic odor.

A major problem is the ability to efficiently and effectively separate the principal alkaloids as well as separate the principal alkaloids from the opium residue. There are a number of methods for separating opium into the principal alkaloids, i.e., morphine, codeine, oripavine, thebaine, papaverine and narcotine. However, all of these techniques are vastly improved by starting with material that is rich in the principal alkaloids with minimal opium residue and other alkaloids. The most common process to separate narcotic alkaloids, which includes morphine, codeine, oripavine, thebaine, papaverine and narcotine (noscapine), is by solvent extraction. Separation includes both purification as well as color removal. The separated narcotic alkaloids are then purified by carbon adsorption and precipitation.

One specific example of this type of modified solvent extraction is found in U.S. Pat. No. 6,054,584 issued to Ma, et al. on Apr. 25, 2000, which discloses a process for extracting only morphine from opium wherein the opium is dissolved in a basic alcoholic solution. The basic alcoholic solution is then filtered and the alcohol is removed from the filtrate to leave a residue. The residue is then extracted with a basic aqueous solution having a pH of at least 11. The basic aqueous solution may be filtered to remove any solid matter remaining after the aqueous extraction step, and then is stirred with a sufficient amount of salt to avoid the formation of an emulsion. The basic aqueous solution or filtrate is then extracted with benzene or toluene. Next, the pH of the basic aqueous filtrate is adjusted to a pH of between 8.5 to 9.5 that allows the morphine to precipitate for recovery.

There are a number of different ways to achieve adsorption besides the use of carbon. One way to achieve adsorption is through ion exchange. Yet another way to achieve adsorption is through polar interaction or normal phase adsorption. Still, yet another way to achieve adsorption is through separating alkaloids from other components based on molecular size by utilizing a membrane.

Another major method for processing opium to separate the principal alkaloids is based on dispersion of opium in water, which is then followed by extraction with hydrochloric acid. This then is followed by separation of the insoluble material with plate-and-frame filtration. This is then followed by separation of morphine and codeine from the other principal alkaloids by extraction with chloroform. The aqueous morphine and codeine stream is treated with lime to remove meconic acid. Morphine is then purified using multiple recrystallizations. Morphine and codeine are then separated by extraction with toluene, then the aqueous morphine stream is extracted with fusel oil. The remaining alkaloids are separated from the chloroform by acid extraction and evaporation. The narcotine, papaverine and thebaine are then obtained by fractional crystallization.

The preferred method for separating the principal alkaloids is by using preparative liquid chromatography. This method includes loading a stationary phase media into a chromatographic column, feeding a crude narcotic alkaloid solution into the chromatographic column, applying at least one mobile phase to the chromatographic column, and recovering at least one narcotic alkaloid eluate from the chromatographic column. This method is disclosed in International Patent Application No. WO03074526 that was published on Sep. 12, 2003, which is incorporated herein by reference in its entirety.

The present invention is directed to overcoming one or more of the problems set forth above.

SUMMARY OF INVENTION

In one aspect of this invention, a method for extracting at least one alkaloid from opium is disclosed. This method includes dissolving opium in a solvent, heating the dissolved opium solution, cooling the dissolved opium solution, adjusting the pH of the dissolved opium solution with one or more somewhat strong to weak acids to improve the filterability of the opium, and to extract the useful alkaloids, cooling to a lower temperature to further improve the filterability, filtering the dissolved opium solution to form a filter cake, and then washing the filter cake to recover more dissolved alkaloids. The spent filter cake may be discarded. The filtrate and wash liquors are then further processed to recover purified morphine, codeine, thebaine, and narcotine. The pH of the acid can vary greatly, however, the use of strong acids (for example, hydrochloric acid) is typically avoided in order to improve yields.

These are merely some of the innumerable aspects of the present invention and should not be deemed an all-inclusive listing of the innumerable aspects associated with the present invention. These and other aspects will become apparent to those skilled in the art in light of the following disclosure and accompanying drawings.

BRIEF DESCRIPTION OF THE DRAWINGS

For a better understanding of the present invention, reference may be made to the accompanying drawings in which.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures and compartments have not been described in detail so as to obscure the present invention.

There are two important operations involved in the separation of principal alkaloids, i.e., morphine, codeine, oripavine, thebaine, papaverine and narcotine. The first is a filtration step to separate the alkaloid-containing filtrate from the insoluble opium residue. A model for constant-pressure batch filtration may be represented as:

$$\frac{dt}{dV} = K_p + B$$

$$K_p = \frac{\mu \alpha C_s}{A^2(\Delta P)}$$

$$B = \frac{\mu R_m}{A(\Delta P)}$$

The filtration area is indicated by variable "A" that is preferably in square meters. The resistance parameter of the opium cake is indicated by variable "$K_p$" that is preferably in seconds/meters$^6$. Pressure is indicated by variable "P" that is preferably in Newtons/meters$^2$. The variable "$R_m$" indicates media resistance that is preferably in 1/meter. The variable "t" is elapsed time that is preferably in seconds. The variable "V" is volume that is preferably in cubic meters. The variable "$\alpha$" indicates opium cake resistance that is preferably in meters/kilogram and the variable "$\mu$" indicates viscosity of the filtrate and is preferably in Newton-second/meter$^2$. The variable "cs" represents the solids concentration in the slurry to be filtered, and is preferably in kg of solids per cubic meter. Finally, variable "B" is the media resistance parameter in the filtration equation that is preferably in seconds/meters$^3$.

Therefore, with a constant pressure batch filtration experiment, a plot of t/V versus volume reveals a linear, straight-line, equation with a slope "$K_p/2$" and an intercept "B." If the liquid viscosity, filter area, solids concentration in the slurry and pressure drop across the filter are known, one can solve for the specific opium cake resistance "$\alpha$" and the media resistance "$R_m$". An illustrative, but nonlimiting, constant-pressure filtration plot is illustrated in FIG. 1.

Figure 1:
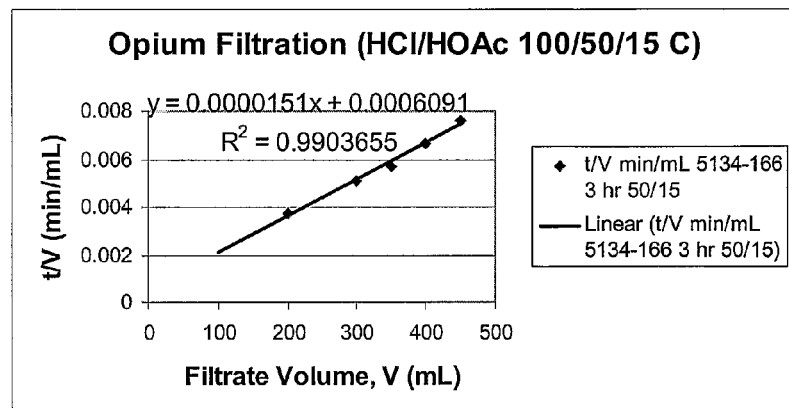
FIG. 1 is a graphical plot of a constant pressure batch filtration experiment, a plot of t/V versus volume.

In the example problem shown in FIG. 1, the solids concentration was found to be 114.32 kg/m$^3$. The viscosity of H$_2$O is 8.937×10$^{-4}$ N s/m$^2$, the pressure drop across the filter is 90,000 N/m$^2$, and filter area was 0.01767 m$^2$. The slope of the line through the data points, Kp/2 is 0.0000151 min/cm$^6$ or 1.812×10$^9$ s/m$^6$. Then solving for the value of opium cake resistance provides the following:

$$\alpha = \frac{(1.812 \times 10^9 \text{ s/m}^6)(0.01767 \text{ m}^2)^2(90,000 \text{ N/m}^2)}{(8.937 \times 10^{-4} \text{ Ns/m}^2)(114.32 \text{ kg/m}^3)} = 4.984 \times 10^{11} \text{ m/kg}$$

the slope of the regression line is linear. This indicates that the opium cake does not become compressed during filtration. Moreover, the binding of the filter media by particulate does not occur.

If the opium cake resistance varies with pressure, the opium cake is compressible. If the opium cake is compressible, increasing the pressure drop across the filter may not result in a proportional increase in filtration rate. The regression line will be curved (nonlinear.) In extreme cases, the flow of filtrate may actually decrease if the pressure is increased too much. Opium cake compression can be caused by the reduction in void volume in the opium cake as the individual particles of opium cake are forced together or by a deformation of particles in the opium cake. Opium cake compressibility can be estimated by performing experiments to determine the relationship between pressure and opium cake resistance ($\alpha = \alpha(\Delta P)$).

Filtration rates can also be adversely affected by blinding of the media by opium particulate. This is most common when the particulate are relatively small compared to the openings in the filter media. This results in the obstruction of the filter media by the particulates.

The problems of opium cake compaction and media blinding may be addressed by several means. Opium cake compaction may be minimized by reducing the pressure drop during the filtration, by adding filter aids, or by chilling the batch to increase the rigidity of the particles. Opium contains tars, which can be made less pliable by reducing the batch temperature during filtration. Media blinding can be reduced by proper selection of media, by pre-coating the media with filter aids, and by back-washing the media between batches to remove embedded fines.

The second major operation involved in the separation of principal alkaloids, i.e., morphine, codeine, oripavine, thebaine, papaverine and narcotine, from opium includes diffusion of the principal alkaloids from within dispersed opium to the surrounding solution. Fick's Second Law of Diffusion can be generally represented as follows:

$$\frac{\partial C_A}{\partial t} = D_{AB} \nabla^2 C_A$$

This equation indicates that the rate of change in concentration of the diffusing alkaloid "A" is proportional to the divergence of the flux of the alkaloid. The variable "$C_A$" is a concentration of the species of alkaloid "A" in moles/meter$^3$. The variable $D_{AB}$ is the diffusivity of the species of alkaloid "A" through species of alkaloid "B" in meters$^2$/second. The variable "t" is elapsed time that is preferably in seconds. It is believed that the flux at the surface of a dispersed opium particle is proportional to the concentration of the alkaloid: ($D_{AB} \nabla C_A = k_L(C_A^{(t,R)} - C_{AL})$). This represents convection, which is either natural or forced, at the surface of the dispersed opium particle. The flux of the alkaloid form the particles of opium at the surface is proportional to the difference in concentration between the bulk liquid phase and the surface of the dispersed opium particle. The proportionality constant "$k_L$" is known as the mass transfer coefficient and is a function of particle size and shape, the physical properties of the flowing fluid and the diffusing specie and the velocity of the flowing fluid relative to the opium particle. Therefore, it is believed based on correlations for estimating mass transfer coefficients that the rate of extraction of the principal alkaloids from the dispersed opium particles increases as the particle size of the opium becomes smaller or the stirring of the opium suspension increases. However, with both processes, there are upper limits. For example, if the opium particulates become too fine, the filtration may become more difficult due to cake compression or blinded filter media.

Other improvements in the extraction of alkaloids may be made by changing the solvents or the temperature. For example, a better choice of acid (or solvent) or increased extraction temperature may increase the mobility of the alkaloids or the solubility of the opium. However, there are two limiting cases that are present. The first case is where diffusion through the particle is slower than the flux at the surface of the particle. This is where the rate of extraction is increased by reducing the particle size and not by increasing the intensity of the mixing. In the second case, diffusion through the particle is faster than the flux at the surface of the particle. This is where the rate of extraction may be increased by stirring and also by reducing the size of the particles.

Experimental Procedure

Typical experiments were conducted with the illustrative, but nonlimiting, equipment. This includes originally dispersing the opium with a blender, e.g., OSTERIZER® dual speed blender. OSTERIZER® is a federally registered trademark of the Sunbeam Corporation, a Delaware corporation, having a place of business at 5400 W. Roosevelt Road, Chicago IL. 60650. The measurement of the blender speed is preferably performed by a tachometer, e.g., Extech Instruments Photo/Contact Tachometer, Model No. 461895. Batch temperatures are measured with a mercury thermometer. The pH is measured with a pH meter that is automatically compensated for temperature. Mixing is performed with a stir/hot plate that utilizes a magnetic stir bar. The filtration is performed with a 15 centimeter (6 inches) Buchner funnel using WHATMAN® No. 40 filter paper unless stated otherwise. WHATMAN® is a federally registered trademark of Whatman International Limited having a place of business at Whatman House, St. Leonard's Road, 20/20 Maidstone Kent, Me16 01s, England. Filtration is also accomplished with a vacuum pump with pressure control, e.g., a BUCHI®E VAC-O-BOX™ or a vacuum pump with vacuum gauges and a manual needle valve to regulate the vacuum. BUCHI® is a federally registered trademark of Buchi Labortechnik AG, a Swiss Corporation, having a place of business at Meierseggstrassse 40, 9230 Flawil, Switzerland.

An illustrative, but nonlimiting, example of a typical experimental batch includes dispersing 119 grams of opium in 500 milliliters of deionized (DI) water, then adjusting the temperature as required. Then, acid is added to obtain a pH of 3.0, then the batch was digested at a specified temperature for a specified period of time. After the digest period has been completed, twenty (20) grams of filter aids are added and the batch is cooled as required. After cooling the suspension, the batch is then filtered. The mother liquor and the cake is then assayed by High Pressure Liquid Chromatography (HPLC) for the principal alkaloids. In some of the experiments, the opium suspension was assayed at intervals following the acid addition in order to obtain the rate of extraction of the principal alkaloids. A wide variety of acids and solvents were tested. In addition, the process temperature was tested over a wide range. Finally, an experiment was conducted to determine the enzymes that were utilized to attempt to destroy some of the constituents that lead to poor filtration.

During the filtration step, the volume of the filtrate and the elapsed filtration time was recorded. A plot of elapsed time in seconds (t)/filtrate volume in cubic meters (V) versus filtrate volume in cubic meters (V) was obtained. The slope of the curve can then be calculated. A pressure drop across the filter is then recorded. After the filtration step is complete, a sample of the opium cake is dried to obtain moisture levels in the opium cake. The solids concentration was then obtained by dividing the number of grams of dry residue by the filtrate volume. The filtrate viscosity is then assumed to be identical to pure water (1cP or $8.937 \times 10^{-4}$ kg/m s.). The specific resistance of the opium cake is then directly computed.

Filtration is also possible with a "pocket filter" that is preferably, but not necessarily, constructed of stainless steel. A pocket filter is configured to perform both pressure and vacuum filtrations. The pocket filter is provided with a jacket and connected to a recirculation heater/chiller to control filtration temperature.

Solution samples were prepared for High Pressure Liquid Chromatography (HPLC) assays by diluting aliquots by a factor of one hundred (100) in a volumetric flask. At first, the solution for diluting samples was preferably, but not necessarily, 50% methanol/50% (1% acetic acid) v/v. However, in this case, the methanol, interfered with the High Pressure Liquid Chromatography (HPLC) method that was adopted to assay narcotine and papaverine. Therefore, the later samples were diluted with a weak acid, e.g., 1% acetic acid. Opium cake samples were prepared by dispersing cake in a volumetric container, e.g., flask, using ultrasound. Aliquots of the opium cake samples were filtered through filters, e.g., 0.45 micron syringe filters, prior to assay.

Some experiments were conducted with solvents to investigate liquid extraction to purify or separate the alkaloids. In these experiments, the aliquot of solvent layer was allowed to evaporate to dryness prior to diluting to volume with the dilute acetic acid. The aliquots were evaporated in this manner to eliminate the effect of solvents on retention time and the peak shape of the chromatography assays. Partition coefficients were obtained by dividing the concentration of the alkaloid in the organic layer by the concentration of the alkaloid in the aqueous layer. The disappearance of the rag layer following liquid extraction was done by filing a mixing container, e.g., cylinder, with the aqueous solution and the solvent. The mixing container, e.g., cylinder is then sealed with a stopper and shook for a predetermined time interval at a certain rate and then recording the interface levels over time.

The results for the opium assay can vary and under certain conditions twin peaks can appear on the chromatogram. As a result, the use of fifty percent (50%) methanol is not preferred. Where it is impossible to obtain a mass balance closure, the assay of the residual alkaloid in the filter cake can be utilized as the benchmark of the process.

Experiment I

The purpose of Experiment I was to obtain side-by-side data of the performance of hydrochloric acid in relationship to acetic acid. The acid digestion occurred at room temperature for 96 hours. The opium suspensions were sampled at intervals, and assays were performed to test the rate of extraction of alkaloids from the opium.

The opium was dispersed by adding one liter of deionized water and 238 grams of opium to the blender. The blender was processed on "puree." This is at 14,046 RPM, or a Reynold's number of 725,791 for two (2) minutes. The slurry was divided between two Erlenmeyer flasks. A tar ball remained in the bottom of the blender. The next step was to add 100 milliliters of water. The blender was then set to "liquefy." This is at 20,495 RPM, or a Reynold's number of 991,216 for thirty (30) seconds. There was not an even distribution between the two Erlenmeyer flasks. This was followed by returning all of the slurry to the blender and processed on "liquefy" for an additional ten (10) seconds. The slurry was then split between the two Erlenmeyer flasks. The slurry was very frothy in appearance. The pH of each Erlenmeyer flask was adjusted to 3.0. In one Erlenmeyer flask, the pH was adjusted with hydrochloric acid (37%), and in the other Erlenmeyer flask, the pH was adjusted with glacial acetic acid. This was followed by withdrawing aliquots and 1.00 gram samples were obtained from each Erlenmeyer flask and filtered through syringe filters. After 96 hours of digestion in acid, 20 grams of filter aids were then added to each Erlenmeyer flask.

The next step was for stirring one hour and then the contents of each Erlenmeyer flask was filtered through two 12.5-cm Buchner funnels that were connected in parallel to a WELCH GEN™ 8890™ vacuum pump. The WELCH GEN™ 8890™ vacuum pump was set to operate at a pressure differential across the filter of 650 millimeters of mercury. The filtration utilizing acetic acid was completed in one (1) hour and twenty-nine (29) minutes. There was 780 milliliters of filtrate collected. The filtration utilizing hydrochloric acid was completed in one (1) hour and forty (40) minutes. There was 560 milliliters of filtrate collected. Samples were collected of each filtrate. These samples were then diluted and then submitted for High Pressure Liquid Chromatography (HPLC) assay.

The opium cakes were then reslurried in water and the pH was adjusted to 3.0. The cakes were then filtered and washed a second time. Moreover, the opium cakes were reslurried, filtered and then washed a third time. All of the filtrates were then sampled and then submitted for High Pressure Liquid Chromatography (HPLC) assay.

Figure 2:
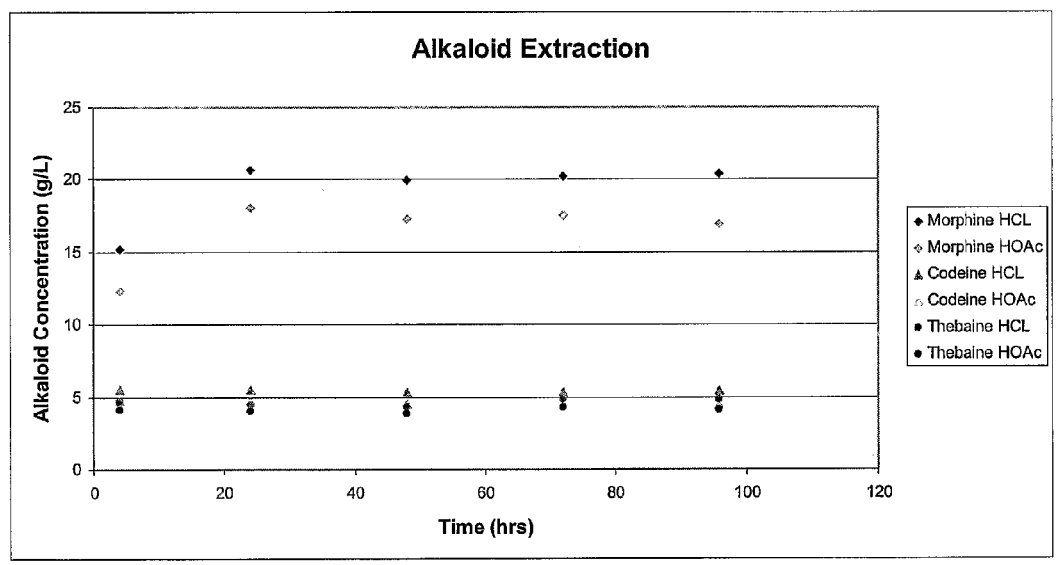
FIG. 2 is a graphical plot of the concentration of alkaloids in the supernatant liquor during the acid digest step comparing hydrochloric acid and acetic acid.

A plot of the concentration of alkaloids in the supernatant liquor during the acid digest step is presented in FIG. 2 comparing hydrochloric acid and acetic acid. The results appear to indicate that all of the alkaloids except for morphine were extracted within four (4) hours (by the first data point). The diffusion of the alkaloids, with the possible exception of morphine, was so fast that it was not possible to obtain data to estimate mass transfer parameters. The morphine extractions were completed in twenty-four (24) hours. Since the concentrations of the alkaloids do not decline over time, these results can also suggest that the alkaloids are stable at room temperature for up to 96 hours when the pH is 3.0.

Referring now to Table 1, the mother liquor assays are presented for each filtration. The yields are based upon an assay performed on a loaf of opium as specified in the United States Pharmacopoeia (USP). There were no detectable alkaloids in either of the filter cakes following the third filtration.

TABLE 1

| | Filtrate Assays (Grams of Alkaloid) | | | | | |
| --- | --- | --- | --- | --- | --- | --- |
| | Morphine | | Codeine | | Thebaine | |
| Filtration | HCL | HOAC | HCL | HOAC | HCL | HOAC |
| 1 | 10.19 | 11.06 | 2.53 | 2.78 | 2.21 | 2.50 |
| 2 | 0.92 | 0.52 | 0.24 | 0.14 | 0.32 | 0.17 |
| 3 | 0.12 | 0.05 | 0.03 | 0.01 | 0.10 | 0.04 |
| TOTAL | 11.23 | 11.63 | 2.81 | 2.93 | 2.63 | 2.72 |
| YIELD | 96.46% | 99.95% | 74.47% | 77.81% | 101.36% | 104.47% |

The next part of the experiment was to test various solvents to identify possible candidates for liquid extraction so that the alkaloids can be separated and purified. There was fifty (50) milliliters of filtrate and fifty (50) milliliters of solvent were charged to one hundred (100) milliliter mixing cylinders. The one hundred (100) milliliter cylinders were shaken for thirty (30) seconds at approximately one (1) shake per second. The one hundred (100) milliliter mixing cylinders were allowed to settle, and the locations of the bottom and top of the rag layer were recorded over time. The results for one trial of the hydrochloric acid extraction of opium is presented in Table 2, and the results of one trial of acetic acid extraction is presented in Table 3. The four solvents used were toluene, hexane, n-butanol (n-BuOH), and isopentyl alcohol (i-C5OH).

TABLE 2

| | Mixing Cylinder Study, Hydrochloric Acid Extract | | | | | | | |
| --- | --- | --- | --- | --- | --- | --- | --- | --- |
| | Upper Emulsion Layer | | | | Lower Emulsion Layer | | | |
| Time (mm:ss) | Toluene | Hexane | n-BuOH | i-C5OH | Toluene | Hexane | n-BuOH | i-C5OH |
| 0:30 | 47 | 70 | | | 47 | 50 | | |
| 1:00 | 47 | 68 | | | 47 | 48 | | |
| 2:00 | 47 | 58 | | | 47 | 48 | | |
| 3:00 | 47 | 54 | 38 | 44 | 47 | 48 | 38 | 44 |
| 4:00 | 47 | 50 | 39 | 45 | 47 | 48 | 39 | 45 |
| 5:00 | 47 | 49 | 40 | 45 | 47 | 49 | 40 | 45 |
| 10:00 | 47 | 49 | 40 | 45 | 47 | 49 | 40 | 45 |

TABLE 3

| | Mixing Cylinder Study, Acetic Acid Extract | | | | | | | |
| --- | --- | --- | --- | --- | --- | --- | --- | --- |
| | Upper Emulsion Layer | | | | Lower Emulsion Layer | | | |
| Time (mm:ss) | Toluene | Hexane | n-BuOH | i-C5OH | Toluene | Hexane | n-BuOH | i-C5OH |
| 0:30 | 51 | 53 | 31 | 35 | 48 | 49 | 31 | 35 |
| 1:00 | 51 | 52 | 32 | 35 | 48 | 49 | 32 | 35 |
| 2:00 | 49 | 51 | 33 | 37 | 49 | 49 | 33 | 37 |
| 3:00 | 49 | 51 | 34 | 40 | 49 | 49 | 34 | 40 |
| 4:00 | 49 | 50 | 35 | 42 | 49 | 49 | 35 | 42 |
| 5:00 | 49 | 49 | 35 | 42 | 49 | 49 | 35 | 42 |
| 10:00 | 49 | 49 | 36 | 43 | 49 | 49 | 36 | 43 |

This data reveals that the emulsion layer in toluene disappears within two (2) minutes and the emulsion layer in hexane disappears within five (5) minutes. The emulsion layer in butanol disappears within three (3) minutes. There is a question as to whether this emulsion layer is present at all since the interface is difficult to view. The emulsion disappears in isopentyl alcohol within a period of three (3) minutes. Once again, there is a question as to whether this emulsion layer is present at all since the interface is difficult to view. The interface between the aqueous phase and the two alcohols continues to drop for about five (5) to ten (10) minutes.

A similar experiment was conducted using chloroform as the organic solvent. In this situation, the interface was very difficult to observe because a thin layer of tar formed on the inside surfaces of the mixing cylinder during the first time that the mixing cylinder was shaken. The result was an emulsion layer that required approximately thirteen (13) minutes to clear from liquors obtained from the acetic acid extraction of the opium. The emulsion cleared within approximately two (2) minutes from liquors obtained from the hydrochloric acid extraction of the opium. This was followed by subsequent shaking, which did not cause the emulsion to re-form. This would appear to suggest that the tars that stabilize the emulsion are irreversibly denatured in the presence of chloroform.

After the mixing cylinder studies were completed, the layers were sampled for High Pressure Liquid Chromatography (HPLC) assay and partition coefficients were obtained for each of the systems. However, at a pH of 3.0, there were no significant concentrations of alkaloid in the toluene or hexane layers. As a result, the partition coefficients are only reported for n-butanol, isopentyl alcohol, and chloroform as shown in Table 4 below:

TABLE 4

Alkaloid Partition Coefficients, pH 3.0

| System | Morphine | Codeine | Thebaine |
| --- | --- | --- | --- |
| BuOH/HCl | 0.1110 | 0.1374 | 0.4312 |
| BuOH/HOAc | 0.1971 | 0.2277 | 0.6351 |
| I-pentyl/HCL | 0.0084 | 0.0181 | 0.1053 |
| I-pentyl/HOAc | 0.0210 | 0.0319 | 0.1548 |
| CHCL3/HCl | 0.0000 | 0.0074 | 0.5363 |
| CHCL3/HOAc | 0.0022 | 0.0341 | 1.5273 |

These results suggest that acetic acid enhances the partitioning of alkaloids into the organic solvent or the acetate salts of the alkaloids are more soluble in solvents than the hydrochloride salts. This would imply that there may be a loss of resolution of the alkaloids during the chloroform extraction if acetic acid is substituted for hydrochloric acid in the step where the opium is dissolved.

The partition coefficients of morphine, codeine, and thebaine were also obtained at a pH of 9.0, by adjusting the pH of a mixture of equal volumes of aqueous solution (opium extracted with acetic acid) and organic solvent. The phases were allowed to separate, and aliquots of each layer were taken. The results are presented in Table 5 below:

TABLE 5

Alkaloid Partition Coefficients, pH 9.0

| System | Morphine | Codeine | Thebaine |
| --- | --- | --- | --- |
| BuOH/HOAc | 8.1095 | 18.9714 | 34.7434 |
| I-pentyl/HOAc | 5.3848 | 19.6646 | 55.5035 |

TABLE 5-continued

Alkaloid Partition Coefficients, pH 9.0

| System | Morphine | Codeine | Thebaine |
| --- | --- | --- | --- |
| Toluene/HOAc | 0.0352 | 5.3686 | 154.6710 |
| Hexane/HOAc | 0 | 0.0735 | 1.8589 |

In the toluene system, the entire organic layer was emulsified with a slight tarry residue in the aqueous layer. In the hexane system, a layer of gum formed at the liquid interface that would disappear upon shaking. A moderate layer of tar formed in the aqueous phase. In the butanol system, the interface is difficult to discern since each phase is equally dark. However, no emulsion or tar would appear to be present. In the isopentyl alcohol system, there was an emulsion in the organic layer. Both phases were dark in color. These high partition coefficients suggest that either n-butanol or i-pentyl alcohol could be used to extract alkaloids from opium.

Experiment II

In this experiment, an attempt was made to extract alkaloids from opium under alkaline conditions with n-butanol and i-pentyl alcohol. There were 237 grams of opium and 500 milliliters of deionized (DI) water were charged to the blender. The opium was processed on a setting of "puree." This was at a speed of 14,046 RPM or a Reynold's number of 679,329 for one minute. The blender was then set to "Mix." This was a speed of 16,283 RPM or a Reynold's number of 787,536 for one (1) minute. The blender was then set to "Liquefy" for thirty (30) seconds. Then, approximately 450 milliliters of slurry was transferred to each of two Erlenmeyer flasks. This was followed by adding 500 milliliters of n-butanol to one flask, and 500 milliliters of i-pentyl alcohol to the other flask. The pH of each flask was adjusted to 9.0 while stirring. The stirring was for one (1) hour and then the samples of the organic layer were collected. The flasks stirred at room temperature for twenty-four (24) hours, then twenty (20) grams of filter aids was added to each flask. The flasks were filtered after one additional hour of stirring. Filtration was done with 12.5 centimeter Buchner funnels with WHATMAN® No. 40 filter paper.

The vacuum pump was adjusted to 650 millimeters of mercury. The filtration times were one (1) hour and nineteen (19) minutes for the butanol flask, and two (2) hours and seventeen (17) minutes for the pentyl alcohol flask. The filtrate volumes were 750 milliliters and 800 milliliters, respectively. The filter cakes were each reslurried in 250 milliliters of water, then 500 milliliters of fresh solvent was added. Then, ten (10) grams of filter aids was added to each flask. Then, each flask was stirred for one hour and then filtered. This was repeated for a third filtration. The second and third filtrations of the n-butanol extraction were complete in approximately one (1) hour each, while the second and third filtrations of the i-pentyl alcohol extraction required approximately four (4) hours each. Aliquots of each phase were taken and submitted for analysis.

Figure 3:
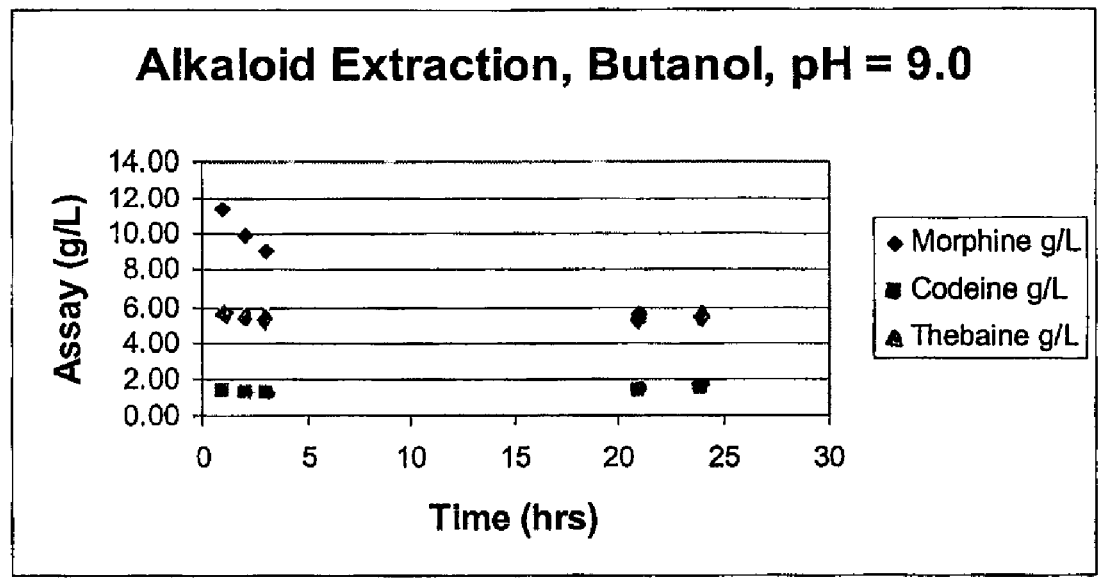
FIG. 3 is a graphical plot of alkaloid extraction with butanol at a pH of 9.0 of the assay (g/L) versus time in hours.

The analytical results reveal that morphine decomposed during the extraction step. Subsequent investigation revealed that morphine is very unstable when the pH was greater than six (6) in the presence of oxygen as shown in FIG. 3 These results tell us that about half of the morphine originally present decomposed after twenty-four (24) hours. The yields of morphine and codeine were only forty percent (40%) to sixty percent (60%) of theoretical exceptions. The combination of long filtration times and poor yields suggests that neither of these methods would scale to a successful commercial process. However, the alkaloid partition coefficients in toluene has proven to be useful in other aspects of the opium process. The concentrations of codeine and thebaine do not change after the first hour, which suggests that mass transfer is complete within one (1) hour. Again, the diffusion of these two alkaloids is so fast that it was not possible to obtain the diffusion parameters.

Experiment III

The first step was to add 119 grams opium and 300 milliliters deionized (DI) water to a blender. The blender was set to "Liquefy." Then, slurry was transferred to an Erlenmeyer flask. This was followed by rinsing the blender with two (2) 100 milliliter washes with deionized (DI) water while processing the blender on "Liquefy" for each wash. Both washes were transferred to the Erlenmeyer flask. The pH was adjusted to 3.03 using 125 milliliters of glacial acetic acid. This was stirred overnight at room temperature. This was followed by adding 20 grams of filter aids, then filtered through a 12.5 centimeter Buchner funnel. The filtration was very slow at approximately fifteen (15) minutes per one hundred (100) milliliters of filtrate. Then, fifty (50) milliliters of filtrate and an equal volume of water was added to an Erlenmeyer flask. This was followed by adding one hundred (100) milliliters of toluene to the flask. Then one (1) gram of ammonium sulfate was added. The pH was adjusted to 10.0 with 1:2 fifty percent (50%) sodium hydroxide: water (v/v.). This was filtered through a 12.5 centimeter Buchner funnel with WHATMAN® No. 40 filter paper.

Even after filtering the batch, the toluene layer appeared completely emulsified. The filtrate was transferred to a separatory funnel and the layers were allowed to separate. The pH of the aqueous layer was adjusted to 3.6 using 35 milliliters of 5:25 concentrated sulfuric acid: water (v/v.) The toluene layer was back-extracted with 100 milliliters of 5% acetic acid (v/v.).

The opium feed solution was almost black in color and opaque. The aqueous layer from the toluene acid extraction was a clear, pinkish-brown color, about the color of dilute tea. The High Pressure Liquid Chromatography assays revealed that the feed solution was only fifteen (15) area percent (%) thebaine, but the aqueous layer from the toluene acid extraction was fifty-five (55) area percent (%) thebaine and twenty-eight (28) area percent (%) codeine. Although the emulsions are present, it does suggest that thebaine can be partially purified, and that the majority of the color may be removed using liquid extraction.

Experiments IV-XXIII—Opium Dispersion

The purpose of these experiments was to test various acids and conditions for the extraction and filtration of opium. The acids tested were acetic acid, hydrochloric acid, formic acid, phosphoric acid, sulfuric acid, mixed formic and acetic acids, and mixed hydrochloric and acetic acids. The experimental conditions included the duration of the digest step, the pretreatment temperature, the digest temperature, and the filtration temperature. Summaries of the experimental conditions and filtration data are presented in Table 6. The opium extraction and filtration process is divided into the following steps: (1) pretreatment, which includes dispersion with a blender, or thermal treatment; (2) the acid digest step; and (3) the filtration step.

TABLE 1

Filtration Data

| Experiment | Pre-Treatment* | Digest Time (hr), Temperature | Acid | Filtration Temp. | Cake Resistance ($10^{13}$ m/kg) | Cake LOD (%) |
|---|---|---|---|---|---|---|
| Exp. IV | Liquefy 1 | 24 | HOAc | | 4.79 | |
| Exp. V | Liquefy 5 | 48 | HOAc | | 4.71 | |
| Exp. VI | Mix, ½ | 2 | HOAc | | 7.03 | 56.2 |
| Exp. VII | Mix, ½ | 24 | HCl | | 0.38 | 49.0 |
| Exp. VIII | Mix, ½ | 96 | HOAc | | 1.32 | 41.4 |
| Exp. IX | Mix, 1 | 24 | Formic | | 0.73 | 49.4 |
| Exp. X | Mix, 1 | 3 | Formic | | 1.47 | 60.4 |
| Exp. XI | Mix, 1 | 3 | Phosphoric | | 1.05 | 56.8 |
| Exp. XII | Mix, ½ | 24 | Sulfuric | | 1.08 | 63.4 |
| Exp. XIII | Mix, ¾ 90 C. | 3 (50 C.) | Formic + 1% HOAc | 25° C. | 0.36 | 49.0 |
| Exp. XIV | Mix, ¾ 70 C. | 3 (50 C.) | Formic + 5% HOA | 50° C. | 0.66 | 60.6 |
| Exp. XV | Mix, ¾ | 3 (50 C.) | Formic | 53° C. | 0.48 | 67.0 |
| Exp. XVI | Mix, ¾ 70 C. | 2 (50 C.) | Formic + 1% HOA | 50° C. | 0.42 | 73.4 |
| Exp. XVII | Boil | 3 (70 C.) | Formic + 1% HOA | 35° C. | 0.041 | 40.4 |
| Exp. XVIII | | 3 (70 C.) | Formic + 1% HOA | 25° C. | 0.51 | 56.8 |
| Exp. XIX | Boil | 3 (70 C.) | Formic + 1% HOAc | 25° C. | 0.048 | 47.0 |
| Exp. XX | Boil | 3 (50 C.) | Formic + 1% HOAc | 15° C. | 0.070 | 50.0 |
| Exp. XXI | Boil | 3 (30 C.) | Formic + 1% HOAc | 15° C. | 0.388 | 56.6 |
| Exp. XXII | Boil | 3 (50 C.) | HCl + 1% HOAc | 5° C. | 0.050 | 38.3 |
| Exp. XXIII | Boil | 3 (40 C.) | Formic + 1% HOAc | 10° C. | 0.158 | 56.6 |
| Exp. XXIV | Boil | 3 (55 C.) | Formic + 1% HOAc | 10° C. | 0.038 | 54.6 |

One of the original concepts investigated was the effect of the particle-size distribution of opium particles upon the filtration rate by using blending. The experimental procedure was to process the charge of opium in a blender at various rotational speeds and durations. The two rotational speeds used were setting the blender to "Liquefy," which was at 20,495 RPM, or a Reynold's number 991,216 and setting the blender to "Mix," which was at 16,283 RPM, or a Reynold's number of 787,536. The data from Experiments IV and V suggest that the duration of blending has no significant affect upon cake resistance. The cake resistance in Experiments VI and VII brackets that of the first two experiments. This suggests that the digest time has a greater effect upon cake resistance than the blending speed or duration of the blending. Blending could also produce highly non-homogeneous suspensions of opium, as moderate-sized pieces (up to two (2) centimeters in diameter) could reside beneath the blades. These opium pieces required manual effort to break free of the blender base, and additional blending time to disperse. However, it becomes apparent by Experiment XVII that opium would disperse upon heating. It was only necessary to cut the raw opium into pieces that would fit through the neck of the Erlenmeyer flask, if the suspension was heated sufficiently.

One of the major results of this investigation was the effect that thermal pre-treatment of the opium has upon the filtration. The opium tends to disperse and dissolve into a very fine suspension with stirring above 70° Celsius. As a result, it was only necessary to cut raw opium into one (1) centimeter to two (2) centimeter pieces that would fit through the neck of the flask used for the dissolving step. There are practical limits to the size of the opium pieces. The raw opium is packaged in wrappings of newsprint, glacine paper, and brown paper bags. These wrappings must be reduced in size to the point that they will not obstruct the equipment as well as expose the opium to the water and acid used for the processing. As a result, it will probably still be necessary to shred the raw opium using, for example serrated agitator.

A second effect of the thermal pre-treatment is to denature some of the constituents in raw opium that obstruct the filtration. Experiments XIII, XVI and XX indicate that as the pre-treatment temperature increases, the cake resistance decreases. In fact, the cake resistance was reduced by a factor of 6.8 between a pre-treatment temperature of 50° Celsius and boiling for fifteen (15) minutes. A portion of this effect is also due to a lower filtration temperature.

A variety of acids were used to extract the alkaloids from opium. The extractions performed with a strong acid, i.e., hydrochloric acid, filters easier than extractions performed with a weak acid, i.e., acetic acid. Sulfuric acid and phosphoric acid produce filter cakes with resistances that are between those obtained with hydrochloric acid and acetic acid. Formic acid with 1% acetic acid was able to produce filter cakes with less resistance than pure formic acid or formic acid and five percent (5%) acetic acid. However, this may also be partly due to the pre-treatment temperature.

These results indicated that as the acid digest time increases, the cake resistance decreases. The cake resistance of extractions was performed with acetic acid is $7.03 \times 10^{-13}$ m/kg following a two hour digest (see Experiment VI), $4.79^{-13}$ m/kg following a 24 hour digest (see Experiment IV) and $1.32^{-13}$ m/kg following a 96-hour digest (see Experiment VIII). In a similar manner, the cake resistance of extractions performed with formic acid decreases by half as the digest time increases from three (3) hours to twenty-four (24) hours. See Experiments IX and X.

The effects of the acid and the digest time suggest that some constituents in opium that restrict filtration are denatured by exposure to acid, and the longer the exposure or the stronger the acid, the more completely denatured these components will become. There also appears to be some benefit to having a small amount of acetic acid present. This might be due to solvent properties of acetic acid. However, in large quantities, i.e., five percent (5%) acetic acid or greater, the cake resistance increases. This suggests that the combination of a moderately strong acid, and a weak acid with some good organic solvent properties, produces the best filter cake.

Figure 4:
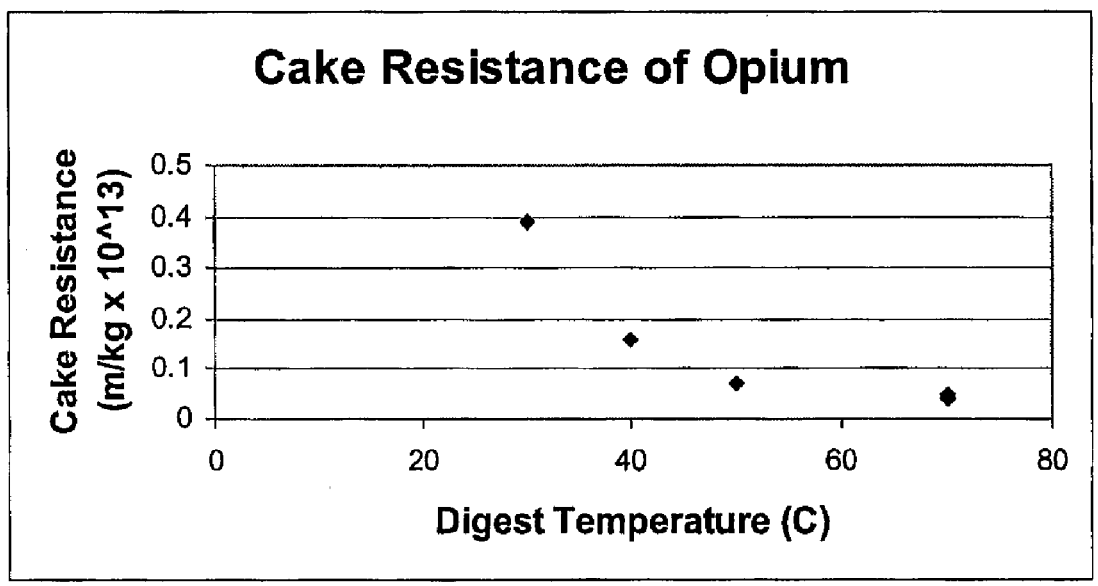
FIG. 4 is a graphical plot of the affect of acid digest temperature upon opium cake resistance.

Increasing the acid digest temperature reduces the cake resistance. See Experiments XVII, XIX, XXI, XXII and XXIII, as shown in FIG. 4. These data suggest that the cake resistance is very sensitive to the digest temperature below 50° Celsius, but the cake resistance is insensitive to digest temperature above 50° Celsius. These data are all based upon pre-treatment of opium by boiling, then digesting three (3) hours in formic acid and one percent (1%) acetic acid.

The opium filter cake is fairly pliable under the best of circumstances. As a result, excessive pressure may be able to cause the cake to compress, and thereby increase the resistance to the flow of filtrate. Tests conducted on-site with a pocket filter, as described later below, revealed that the cake resistance decreases as the temperature is reduced. The data suggest that at temperatures at or below 15° Celsius, the cake resistance decreases. This suggests that the opium cake becomes more rigid with less compaction at temperatures below 15° Celsius.

The percentage of recovered alkaloid in the filtrate is presented below in Table 7. This value represents the percentage of recovered alkaloid that is in the filtrate. This recovered alkaloid includes alkaloid in the filtrate and residual in the opium cake. This is a measure of the efficiency of the extraction and opium cake wash. However, the washes were not done with large quantities of water. They were typically done with relatively small quantities of water (2×50 milliliters). The purpose of these experiments was to provide indications of conditions that produce favorable or unfavorable filtration efficiencies.

The experimental data suggests that pretreatment by boiling increases the recovery of the alkaloids from the opium cake. Experiments XVII and XIX had consistently higher recoveries of alkaloid in the filtrate than Experiment XVIII. The duration of the digest (see Experiments VI and VIII) also appears to play an important role, as the longer digest had a higher recovery. It also appears that the use of hydrochloric acid (see Experiment XXII) does not promote as efficient a recovery as formic acid. This may suggest that the somewhat superior solvent characteristic of formic acid is beneficial to the recovery of the alkaloids. However, the digest temperature after boiling the opium suspension (see Experiments XVII, XX, XI and XIII) does not appear to effect the efficiency of the extraction.

TABLE 7

Recovery of Alkaloid From Filter Cake
(Percentage of Recovered Alkaloid in Filtrate)

| Experiment | Morphine | Codeine | Thebaine | Narcotine |
|---|---|---|---|---|
| Exp. VI (HOAC, 2 hr) | 90.4 | 89.2 | 89.3 | |
| Exp. VII (HCl, 24 hr) | 88.2 | 88.1 | 81.2 | |
| Exp. VIIII (HOAc, 96 hr) | 94.8 | 97.3 | 95.1 | 93.7 |
| Exp. IX (Formic, 24 hr) | 94.7 | 93.6 | 89.4 | 87.5 |
| Exp. X (Formic, 3 hr) | 81.6 | 82.1 | 76.8 | 75.8 |
| Exp. XI (Phosphoric, 3 hr) | 82.7 | 82.9 | 76.6 | 75.0 |

TABLE 7-continued

Recovery of Alkaloid From Filter Cake
(Percentage of Recovered Alkaloid in Filtrate)

| Experiment | Morphine | Codeine | Thebaine | Narcotine |
|---|---|---|---|---|
| Exp. XII (Sulfuric, 24 hr) | 87.8 | 88.5 | 80.9 | 79.4 |
| Exp. XIII (Formic + 1% HOAc, 50° C., 3 hr) | 97.0 | 97.6 | 91.0 | 89.5 |
| Exp. XIV (Formic + 5% HOAc, 50° C., 3 hr) | 93.1 | 90.0 | 89.5 | 87.9 |
| Exp. XV (Formic, 50° C., 3 hr) | 93.0 | 93.7 | 87.7 | 85.3 |
| Exp. XVI (Formic + 1% HOAc, 50° C., 2 hr) | 89.8 | 90.6 | 85.0 | 82.5 |
| Exp. XVII (Boil, Formic + 1% HOAc, 70° C., 3 hr) | 97.8 | 98.0 | 93.9 | 92.1 |
| Exp. XVIII (Formic + 1% HOAc, 70° C., 3 hr) | 86.5 | 87.4 | 82.0 | 80.1 |
| Exp. XIX (Boil, Formic + 1% HOAc, 70° C., 3 hr) | 96.2 | 96.1 | 92.3 | 91.4 |
| Exp. XX (Boil, Formic + 1% HOAc, 50° C., 3 hr) | 97.8 | 98.1 | 93.6 | 90.5 |
| Exp. XXI (Boil, Formic + 1% HOAc, 30° C., 3 hr) | 98.0 | 99.9 | 94.1 | 90.6 |
| Exp. XXII (Boil, HCl + 1% HOAc, 50° C., 3 hr) | 90.8 | 91.4 | 83.3 | 69.1 |
| Exp. XXIII (Boil, Formic + 1% HOAc, 40° C., 3 hr) | 98.2 | 100 | 94.5 | 92.1 |

Experiments were then performed with a jacketed stainless steel pocket filter, with a filtration area of 20 square centimeters, a Nitrogen cylinder with a pressure regulator, a BUCHI® VAC-O-BOX™ vacuum pump, and a recirculation chiller/heater. An illustrative, but nonlimiting, jacketed stainless steel pocket bit pocket filter is manufactured by BHS Filtration Inc. having a place of business at 9123-115 Monroe Road, Charlotte, N.C. 28270.

The procedure included making up bulk opium suspension by charging 1,500 milliliters of deionized (DI) water and 357 grams of opium to an Erlenmeyer flask. The flask was boiled gently for approximately fifteen (15) minutes, then cooled to 50° Celsius. After the flask was cooled, 15 milliliters of acetic acid was charged, and the pH was adjusted to 3.0 with formic acid. The flask was stirred for three (3) hours at 50° Celsius, then sixty (60) grams of filter aids was charged. After charging the filter aids, the flask was stirred for one (1) additional hour.

The filtration tests were typically conducted with 100 milliliter aliquots of the opium slurry (Experiment XVIII was conducted with 75 milliliters of slurry.) The opium slurry was charged to the pocket filter, which was provided with filter media. Pressure filtrations were performed by connecting the nitrogen cylinder to the pocket filter, and setting the desired pressure with the regulator. The filtrate was collected in a graduated cylinder and timed with a stopwatch. The vacuum filtration experiments were performed by connecting the VAC-O-BOX™ and the pocket filter to a filter flask. This is followed by timing the flow of filtrate into the vacuum flask.

Then, pressure filtrations were conducted at 1, 2, 3, 4, and 6 bar gauge pressure, and vacuum filtrations were performed at −0.8, −0.84, and −0.91 bar. The washes were typically performed with fifteen (15) milliliters of 1% formic acid.

The data indicated that compaction of the cake occurred under conditions of pressure filtration. Increasing pressure did not lead to a proportional decrease in filtration time. In addition, pressure filtration typically led to eventual blinding of the filter media. The key filtration data for the best trials are summarized below in Table 8:

TABLE 8

BHS Filtration Test Data

| | Experiment | | | | | |
|---|---|---|---|---|---|---|
| | XXV | XXVI | XXVII | XXVIII | XXIX | XXX |
| Pressure (bar) | −0.80 | −0.80 | −0.80 | 3 | 3 | 3 |
| Temperature (C.) | 15 | 30 | 5 | 5 | 5 | 5 |
| Slurry Volume (mL) | 100 | 100 | 100 | 75 | 100 | 150 |
| Filter Time (s) | 960 | 980 | 870 | 320 | 720 | 1920 |
| Wash 1 Time (s) | 350 | 375 | 360 | 40 | 200 | 920 |
| Wash 2 Time (s) | 350 | 605 | 320 | 55 | 92 | abort @1200 |
| Wash 3 Time (s) | 620 | Abort @1200 | 395 | 50 | 120 | |

The data in Table 8 suggests that the relatively high filtration temperature, e.g., 30° Celsius, in Experiment XXVI led to highly restricted filtrate flow. This suggests that the filter cake is still pliable at 30° Celsius, but is less pliable at or below 15° Celsius. The filter media was replaced prior to Experiment XXVII. These results also suggest that vacuum filtration results in extended media life, because there is a very large increase in filtration and wash time between Experiments XXVIII, XIX and XXX. Experiment XXX was conducted under the same conditions as experiments XXVIII and XIX, but was terminated during the second wash due to excessive filtration time. This suggests that although the shortest filtration time was obtained in Experiment XXVIII, an attempt to replicate this experiment with the same media resulted in blinding of the filter media. Experiments XXVI and XXX produced wet filter cake, while the opium cake was relatively dry in all other cases. The opium cake did not appear cracked in any of these Experiments.

The mother liquor and opium cake assays are presented below for these Experiments as shown in Tables 9 through Table 13. The "yield" calculation is based upon the alkaloid recovered in the combined filtrate and washes, divided by the sum of the recovered alkaloid and the residue in the filter cake. The analytical procedures are as follows:

Morphine trifluoroacetic acid (TFA) research method, which applies to dissolved solution.

| | |
|---|---|
| Column: | Waters Symmetry, C18 5-micron, 3.9 × 150 millimeters. |
| Mobile Phases: | A: 0.1% (v/v) trifluoroacetic acid (TFA) in water. B: 0.1% (v/v) trifluoroacetic acid (TFA) in 1:1 water:acetonitrile. |
| Flow Rate: | 1 milliliters/minute. |
| Gradient: | 0-25.5% B over 25 minutes, linear; 25.5-100% B over 15 minutes, linear; re-equilibrate 100-0% B over 1 minute; hold 0% B for 9 minutes. |
| Run Time: | 50 minutes. |
| Column Temperature: | 37° Celsius. |
| Injection Volume: | 10 microliters. |
| Detection: | UV @ 280 nanometers. |
| Sample & Standard Preparation: | 2 mg/mL in 0.1 N sulfuric acid. |

Opium Assay, See as specified in the United States Pharmacopoeia (USP).

Opium filter cake assay/rapid Opium assay. Dry approximately five (5) grams of wet filter cake, accurately weighed, under vacuum at 50°-60° Celsius for at least forty-eight (48) hours. Grind the cake into a fine powder with a metal spatula. Transfer approximately 0.1 grams of dried powder, accurately weighed, into a volumetric flask (100 to 500 milliliters volume.) Add one percent (1%) glacial acetic acid/water (v/v) to just below mark. Disperse with ultrasound. This was allowed to stand at least one (1) hour (preferably overnight). Dilute to mark with one percent (1%) glacial acetic acid. Shake flask thoroughly. Withdraw an aliquot for High Pressure Liquid Chromatography (HPLC) analysis, and filter through a 0.45 micron syringe filter into a High Pressure Liquid Chromatography (HPLC) sample vial. Test the sample by the Morphine TFA Research Method.

TABLE 9

BHS Filtration Morphine Recovery in Filtrate and Washes, and Residue in Cake

| | Experiment | | | | |
|---|---|---|---|---|---|
| | XXV | XXVI | XXVII | XXVIII | XXIX |
| Filtrate (g) | 1.84 | 1.93 | 1.79 | 1.44 | 2.02 |
| Wash 1 (g) | 0.25 | 0.31 | 0.33 | 0.06 | 0.14 |
| Wash 2 (g) | 0.15 | 0.07 | 0.08 | 0.05 | 0.04 |
| Wash 3 (g) | 0.02 | 0.01 | 0.01 | 0.03 | 0.04 |
| Cake (g) | 0.02 | 0.01 | 0.02 | 0.04 | 0.08 |
| Total (g) | 2.28 | 2.33 | 2.22 | 1.62 | 2.32 |
| Yield (%) | 99.25 | 99.37 | 99.26 | 97.32 | 96.54 |

TABLE 10

BHS Filtration Codeine Recovery in Filtrate and Washes, and Residue in Cake

| | Experiment | | | | |
|---|---|---|---|---|---|
| | XXV | XXVI | XXVII | XXVIII | XXIX |
| Filtrate (g) | 0.55 | 0.58 | 0.53 | 0.43 | 0.60 |
| Wash 1 (g) | 0.08 | 0.09 | 0.10 | 0.02 | 0.04 |
| Wash 2 (g) | 0.05 | 0.02 | 0.03 | 0.01 | 0.01 |
| Wash 3 (g) | 0.01 | 0.00 | 0.00 | 0.01 | 0.01 |
| Cake (g) | 0.00 | 0.00 | 0.00 | 0.01 | 0.02 |
| Total (g) | 0.68 | 0.70 | 0.66 | 0.48 | 0.68 |
| Yield (%) | 100.00 | 100.00 | 100.00 | 97.34 | 96.65 |

TABLE 11

BHS Filtration Thebaine Recovery in Filtrate and Washes, and Residue in Cake

| | Experiment | | | | |
|---|---|---|---|---|---|
| | XXV | XXVI | XXVII | XXVIII | XXIX |
| Filtrate (g) | 0.34 | 0.36 | 0.38 | 0.31 | 0.43 |
| Wash 1 (g) | 0.06 | 0.07 | 0.07 | 0.01 | 0.03 |
| Wash 2 (g) | 0.04 | 0.03 | 0.03 | 0.01 | 0.01 |
| Wash 3 (g) | 0.02 | 0.01 | 0.02 | 0.01 | 0.01 |
| Cake (g) | 0.01 | 0.00 | 0.02 | 0.03 | 0.05 |
| Total (g) | 0.46 | 0.47 | 0.52 | 0.37 | 0.53 |
| Yield (%) | 98.67 | 98.98 | 97.12 | 91.42 | 90.05 |

TABLE 12

BHS Filtration Papaverine Recovery in Filtrate and Washes, and Residue in Cake

| | Experiment | | | | |
|---|---|---|---|---|---|
| | XXV | XXVI | XXVII | XXVIII | XXIX |
| Filtrate (g) | 0.36 | 0.38 | 0.34 | 0.27 | 0.38 |
| Wash 1 (g) | 0.05 | 0.06 | 0.07 | 0.01 | 0.03 |
| Wash 2 (g) | 0.03 | 0.02 | 0.02 | 0.01 | 0.01 |
| Wash 3 (g) | 0.01 | 0.01 | 0.01 | 0.01 | 0.01 |
| Cake (g) | 0.04 | 0.03 | 0.05 | 0.04 | 0.07 |
| Total (g) | 0.48 | 0.50 | 0.49 | 0.34 | 0.49 |
| Yield (%) | 92.44 | 93.40 | 88.89 | 87.08 | 85.80 |

TABLE 13

BHS Filtration Narcotine Recovery in Filtrate and Washes, and Residue in Cake

| | Experiment | | | | |
|---|---|---|---|---|---|
| | 16 | 17 | 18 | 19 | 20 |
| Filtrate (g) | 0.76 | 0.81 | 0.73 | 0.59 | 0.83 |
| Wash 1 (g) | 0.11 | 0.14 | 0.14 | 0.03 | 0.06 |
| Wash 2 (g) | 0.08 | 0.07 | 0.07 | 0.02 | 0.02 |
| Wash 3 (g) | 0.05 | 0.03 | 0.04 | 0.01 | 0.01 |
| Cake (g) | 0.02 | 0.02 | 0.06 | 0.07 | 0.11 |
| Total (g) | 1.03 | 1.06 | 1.04 | 0.71 | 1.04 |
| Yield (%) | 97.74 | 98.07 | 94.50 | 90.64 | 89.24 |

The material balance data suggests several important results. First, the higher-pressure filtration and washes have lower recoveries of all of the alkaloids, particularly thebaine, papaverine, and narcotine. Although pressure filtrations and washes are initially much faster than vacuum filtrations, the media becomes blinded, leading to greatly increased filtration and wash times for subsequent batches. Second, the higher temperature filtration (35° Celsius) had the longest vacuum filtration and wash times. Third, the lower temperature vacuum filtration (5° Celsius) had a somewhat lower recovery of thebaine, narcotine, and papaverine. This data suggests that the optimal filtration conditions are vacuum filtration at approximately −0.8 bar, and 15° Celsius.

Extraction Process

The optimal quantities used for commercial batches are presented in Table 14 as contrasted to laboratory batches.

TABLE 14

Contrasting Lab and Proposed Plant Batch Sizes

| Component | U/M | Lab | Plant |
|---|---|---|---|
| Opium | kg | 0.119 | 540 |
| Water | L | 0.5 | 2269 |
| Acetic Acid | L | 0.005 | 22.7 |
| Formic Acid | L | 0.01 | 45 |
| Filter Aids | kg | 0.02 | 91 |
| Wash | L | 0.3 | 1361 |
| Filtrate | L | 0.8 | 3630 |
| Morphine | kg | 0.01407 | 63.9 |
| Codeine | kg | 0.00435 | 19.7 |
| Thebaine | kg | 0.0036 | 16.3 |
| Papaverine | kg | 0.00308 | 14.0 |
| Narcotine | kg | 0.00667 | 30.3 |

The proposed commercial process includes:

1. Charge from about 1,135 liters to about 3,404 liters, and preferably from about 1,702 liters to about 2,836 liters and optimally 2,269 liters of solvent, e.g., deionized (DI) water, to the vessel, e.g., dissolver. Illustrative, but nonlimiting example of a solvent can include water. A wide variety of vessels provided with an agitator will suffice with the preferred vessel being a dissolver.

2. Begin heating the vessel, e.g., dissolver. Preferably, but not necessarily, the vessel is not brought to boiling until all the opium has been added. Charge from about 270 kilograms to about 810 kilograms, and preferably from about 405 kilograms to about 675 kilograms and optimally 540 kilograms of opium to the vessel, e.g., dissolver.

3. Continue to heat the vessel, e.g., dissolver while stirring vigorously to break up insoluble matter. Heating is from about 70° Celsius to about 105° Celsius, and preferably from about 95° Celsius to about 105° Celsius and optimally brought to boiling from about 100° Celsius to about 105° Celsius.

4. Boil for about 0 minutes to about 60 minutes, and preferably from about 5 minutes to about 30 minutes and optimally boil with gentle heating for 5 minutes to 15 minutes.

5. Cool the vessel, e.g., dissolver, from about 25° Celsius to about 70° Celsius, and preferably from about 40° Celsius to about 60° Celsius and optimally from about 50° Celsius to about 55° Celsius.

6. Charge from about 1 liter to about 227 liters, and preferably from about 1 liter to about 114 liters and optimally 22.7 liters of a weak acid, e.g., glacial acetic acid.

7. Adjust the pH of the vessel, e.g., dissolver from about 0 pH to about 4 pH, and preferably from about 1 pH to about 4 pH and optimally to 3.0 with a moderately strong acid, e.g., formic acid, e.g., 88% formic acid. This will require from about 165 liters to about 0 liters, and preferably from about 56 liters to about 0 liters and optimally about 45 liters of acid. Weak acids include, but are not limited to acetic acid, formic acid, carbonic acid, citric acid, propionic acid, trichloroacetic acid, hydrocyanic acid, pyruvic acid and conjugate acids of weak bases.

8. Stir with a stirring mechanism from about 1 hours to about 12 hours, and preferably from about 2 hours to about 4 hours and optimally for 3 hours from about 25° Celsius to about 70° Celsius, and preferably from about 40° Celsius to about 60° Celsius and optimally from about 50° Celsius to about 55° Celsius.

9. Optimally, check the pH periodically and add additional weak acid, e.g., formic acid as needed.

10. Charge from about 46 kilograms to about 137 kilograms, and preferably from about 68 kilograms to about 114 kilograms and optimally 91 kilograms of filter aids, and stir for one hour. Illustrative filter aids include, but are not limited to, diatomite, perlite, dicalite, vegetable grain, diatomaceous earth, calcium silicate, magnesium silicate, amorphous silicas and cellulose.

11. Cool from about 0° Celsius to about 30° Celsius, and preferably from about 0° Celsius to about 25° Celsius and optimally from about 5° Celsius to about 15° Celsius.

12. Filter the batch using a vacuum filter set to a differential pressure from about 0 bar to about 1 bar, and preferably from about 0.5 bar to about 1 bar and optimally −0.8 bar. Filtering can be performed with a horizontal belt filter that operates under a vacuum.

13. Wash the cake from about 136 liters to about 2000 liters, and preferably from about 1000 liters to about 1500 liters and optimally 1361 total liters of an acidified solvent, e.g., dilute formic acid. Dilute formic acid should have a pH of 3.0, and contains approximately 0.3 grams of acid per liter of solution. The acidified solvent includes a solvent the includes, but is not limited to water, and the acid is selected from the group consisting of acetic acid, formic acid, carbonic acid, citric acid, propionic acid, trichloroacetic acid, pyruvic acid and conjugate acids of weak bases.

14. Separate and purify the alkaloids in the filtrate and wash with either preparative liquid chromatography, e.g., High Pressure Liquid Chromatography (HPLC), or solvent extraction and filtration among other techniques.

Opium is a semi-solid at room temperature in an aqueous dispersion. At approximately 70° Celsius, the opium begins to dissolve or disperse in water. At temperatures above approximately 30° Celsius, components of opium that cause slow filtration rates begin to denature. These components (which cause the filter cake to be somewhat gelatinous in nature) denature to an increasing extent at the temperature is increased, and rapidly denature upon boiling. A heavy, sticky foam forms at the onset of boiling, and care must be taken to ensure that the process vessel does not foam over. Spraying deionized water into the batch may disperse the foam. The foam also disappears after boiling for about fifteen (15) minutes. There does not appear to be an advantage to boiling the opium suspension for a longer duration.

Digesting at elevated temperatures after the acid addition also reduces the cake resistance of opium as shown in FIG. 4. However, there is little improvement in cake resistance above 50° Celsius. As a result, satisfactory filtration occurs at a digest temperature of 50° Celsius to 55° Celsius. It is not recommended to digest above 55° Celsius, in case the combination of acidic conditions and high temperatures result in loss of thebaine. If too much acid is added, the pH may be raised by adding base (sodium carbonate or sodium hydroxide.) There does not appear to be any benefit to extending the digest time beyond three (3) hours. There does not appear to be any significant loss of morphine, codeine, or thebaine at room temperature at pH 3.0 for up to ninety-six (96) hours.

The particular acid or mix or acids is important. The gelatinous components of opium denature somewhat rapidly (without boiling, and at room temperature) in hydrochloric acid (twenty-four (24) hours), at a moderate rate in formic acid (twenty-four (24) hours) and slowly in acetic acid (ninety-six (96) hours.) However, acetic acid appears to help leach the desired alkaloids from the raw opium. The best mix of acids identified was to first add acetic acid to the batch in order to make up a one percent (1%) solution by volume, and then add formic acid to obtain a pH of 3.

Filter aids are added prior to cooling the batch. This introduces nucleation sites for collecting tars in the event that some tars precipitate from solution upon cooling. Two aspects may be observed during filtration. If the temperature is high (20° Celsius or above) the opium cake becomes somewhat soft, and causes an increased cake resistance. If the temperature is too low (5° Celsius or below) the filtrate may become somewhat frothy. As a result, the filtration temperature of 5° Celsius to 15° Celsius is preferred.

Therefore, a process has been developed on the laboratory scale which extracts alkaloids from opium with greater than ninety-six percent (96%) efficiency, and which has a lower cake resistance than the existing processes. The new process uses weaker acids (formic and acetic acids) than the existing plant process (in which hydrochloric and acetic acids are used.) The new process employs a thermal pre-treatment of the opium slurry (boiling for 15 minutes) which denatures some of the constituents in opium that restrict filtration. Heating the opium solution also increases the solubility of the opium. The combination of formic and acetic acids also appears to improve the extraction efficiency of the alkaloids. A minimum temperature for the acid extraction step is 50° Celsius, as this produces filter cake with a low resistance. Chilling the cake to 15° Celsius also reduces the tendency of the cake to compress during filtration, thereby reducing the cake resistance. Vacuum filtration in superior to pressure filtration, because pressure filtration causes cake compaction and/or blinding of the filter media.

Although the preferred embodiment of the present invention and the method of using the same has been described in the foregoing specification with considerable details, it is to be understood that modifications may be made to the invention which do not exceed the scope of the appended claims and modified forms of the present invention incorporated by others skilled in the art to which the invention pertains will be considered infringements of this invention when those modified forms fall within the claimed scope of this invention.

The invention claimed is:

1. A method for extracting at least one alkaloid from opium comprising:
dissolving opium in a solvent;
heating the dissolved opium solution to a temperature from about 70° Celsius to about 105° Celsius;
cooling the dissolved opium solution;
adjusting the pH of the dissolved opium solution with at least one weak acid;
filtering the dissolved opium solution to recover a filtrate, and
separating and purifying the at least one alkaloid in the filtrate.

2. The method for extracting at least one alkaloid from opium as set forth in claim 1, further comprising chilling the opium solution after the adjusting the pH of the dissolved opium solution with at least one first acid.

3. The method for extracting at least one alkaloid from opium as set forth in claim 2, wherein the step of chilling the opium solution is at a temperature from about 0° Celsius to about 30° Celsius.

4. The method for extracting at least one alkaloid from opium as set forth in claim 2, wherein the step of chilling the opium solution is at a temperature from about 0° Celsius to about 25° Celsius.

5. The method for extracting at least one alkaloid from opium as set forth in claim 1, wherein the solvent includes water.

6. The method for extracting at least one alkaloid from opium as set forth in claim 1, wherein the step of heating the dissolved opium solution is at a temperature from about 95° Celsius to about 105° Celsius.

7. The method for extracting at least one alkaloid from opium as set forth in claim 1, wherein the step of cooling the dissolved opium solution is at a temperature from about 25° Celsius to about 70° celsius.

8. The method for extracting at least one alkaloid from opium as set forth in claim 1, wherein the step of cooling the dissolved opium solution is at a temperature from about 40° Celsius to about 60° Celsius.

9. The method for extracting at least one alkaloid from opium as set forth in claim 1, wherein the step adjusting the pH of the dissolved opium solution is in a range from about 2 pH to about 4 pH.

10. The method for extracting at least one alkaloid from opium as set forth in claim 1, wherein the step adjusting the pH of the dissolved opium solution is in a range from about 2.5 pH to about 3.5 pH.

11. The method for extracting at least one alkaloid from opium as set forth in claim 1, wherein at least one weak acid includes acetic acid and formic acid.

12. The method for extracting at least one alkaloid from opium as set forth in claim 1, wherein the at least one weak acid is selected from the group consisting of acetic acid, formic acid, carbonic acid, citric acid, propionic acid, trichloroacetic acid, nicotinic acid, pyruvic acid and conjugate acids of weak bases.

13. The method for extracting at least one alkaloid from opium as set forth in claim 1, wherein after the step of adjusting the pH of the dissolved opium solution further comprises the step of stirring the dissolved opium solution from about 60 minutes to about 720 minutes at a temperature from about 25° Celsius to about 70° Celsius.

14. The method for extracting at least one alkaloid from opium as set forth in claim 1, wherein after the step of adjusting the pH of the dissolved opium solution further comprises the step of stirring the dissolved opium solution from about 120 minutes to about 240 minutes at a temperature from about 40° Celsius to about 60° Celsius.

15. The method for extracting at least one alkaloid from opium as set forth in claim 1, wherein after the step of stirring the dissolved opium solution further comprises the step of adding filter aids to the opium solution.

16. The method for extracting at least one alkaloid from opium as set forth in claim 15, wherein the filter aids are selected from the group consisting of diatomite, perlite, dicalite, vegetable grain, diatomaceous earth, calcium silicate, magnesium silicate, amorphous silicas and cellulose.

17. The method for extracting at least one alkaloid from opium as set forth in claim 1, wherein the filtering of dissolved opium solution to recover a filtrate is under a vacuum.

18. The method for extracting at least one alkaloid from opium as set forth in claim 1, wherein the filtering of the dissolved opium solution to recover a filtrate is done with a horizontal belt filter.

19. The method for extracting at least one alkaloid from opium as set forth in claim 1, wherein the filtering of the dissolved opium solution to recover a filtrate includes forming a filter cake and washing the filter cake with an acidified solvent.

20. The method for extracting at least one alkaloid from opium as set forth in claim 19, wherein the step of washing the filter cake with an acidified solvent is under a vacuum.

21. The method for extracting at least one alkaloid from opium as set forth in claim 20, wherein the acidified solvent includes a solvent, which includes water and the acid is selected from the group consisting of acetic acid, formic acid, carbonic acid, citric acid, propionic acid, trichloroacetic acid, nicotinic acid, pyruvic acid and conjugate acids of weak bases.

22. The method for extracting at least one alkaloid from opium as set forth in claim 1, wherein the step of separating and purifying at least one alkaloid in the filtrate includes utilizing preparative liquid chromatography.

23. The method for extracting at least one alkaloid from opium as set forth in claim 1, wherein the step of separating and purifying the at least one alkaloid in the filtrate includes utilizing solvent extraction and filtration.

* * * * *